US005127396A

United States Patent [19]

McAllister

[11] Patent Number: 5,127,396

[45] Date of Patent: Jul. 7, 1992

[54] PLUG AND PHALLIC DEVICE AND SYSTEM

[75] Inventor: Ron McAllister, North Hollywood, Calif.

[73] Assignee: Health Devices Corporation, N. Hollywood, Calif.

[21] Appl. No.: 707,655

[22] Filed: May 30, 1991

[51] Int. Cl.[5] .................... A61F 5/00

[52] U.S. Cl. .................... 600/38; 128/844

[58] Field of Search .................... 128/32, 79, 842, 844, 128/869, 883; 623/7, 66; 604/345, 346-347, 349, 351, 353; 606/191, 197; 403/298, 253, 267, 333-334, 360-361

[56] References Cited

U.S. PATENT DOCUMENTS 3,485,520 12/1969 Alexander .................... 403/360

4,873,996 10/1989 Maurer .................... 128/844

*Primary Examiner*—Randall L. Green

*Assistant Examiner*—Gina Gualtieri

*Attorney, Agent, or Firm*—Spensley Horn Jubas & Lubitz

[57] ABSTRACT

Disclosed is a system which includes a phallus or other plug receiving device formed of resilient material in combination with a plug formed of a substantially rigid material. A hollow is shaped in the plug receiving devices' back which corresponds to the shape of the plug, but has slightly smaller dimensions. When the plug is forced into the plug receiving devices' hollow, air is expelled from the hollow and a vacuum-like fit is achieved. Preferably, the plug and phallus may be combined with a harness formed of inelastic clothlike material forming the body of the harness, the body having a length sufficient to reach around from the wearer's lower abdomen, between the wearer's legs and up onto or over the wearer's buttocks. Inelastic straps are attached along the ends of the harness body and are adjustably attachable to each other so that the harness may be worn like a bathing suit bottom having fasteners on the sides. The harness body is sufficiently wide at its central portion to avoid binding the wearer, and gradually widens toward each of its ends. The portion of the harness body which would be positioned below the wearer's abdomen has a hole formed in it and means for fastening to a flange formed in the back of the plug. In use the plug is passed through the hole and the plug's flange is attached to the harness; then the plug is forced into the hollow of a plug phallus. Then the harness is put on by the wearer.

31 Claims, 9 Drawing Sheets

PLUG AND PHALLIC DEVICE AND SYSTEM

BACKGROUND OF THE INVENTION

1. Field of The Invention

This invention relates to the field of phallic devices, including prosthetic devices and dildos.

2. Prior Art

Phalluses (or phalli) have been used as penis substitutes from time immemorial. In cultures where hymenal blood was considered evil or dangerous, a husband would avoid his young bride until she attended a ceremony during which her hymen was pierced by a substitute for the husband, often a phallus made of stone, metal, ivory or even wood. In other cultures the deflowering of a young bride by the phallus of a fertility god was part of ceremonies aimed at assuring the procreative success of a married couple. Similar ceremonies were also participated in by long-married wives who were childless. See *Panati's Extraordinary Endings of Practically Everything and Everybody,* Charles Panati (Harper & Row, New York, 1989).

In addition to serving in sacred fertility and marriage ceremonies, phalluses have been used for the simple purpose of pleasure, by couples and by people who are otherwise alone.

Even from earliest times phalluses have been made as simple as an ordinary smooth-edged cylinder, as close replicas of human penises, as reproductions of exaggerated erect penises, or as ornately decorated symbols of the male reproductive organ.

In more recent times, with the development of modern plastics and other moldable materials, phalluses may be mass produced in a wide variety of forms pleasing in shape and design for use as decorative sculptures, or as a device used in erotic activities.

With the onslaught of venereal diseases such as herpes and AIDS, phalluses substitute for the male reproductive organ as part of safe sex practices. Phalluses are also used by couples when the male partner is impotent. And, sex aids and paraphernalia, such as phalluses, have been used by sex counselors as part of the tools used to counsel their patients.

In order to allow users of phalluses to more closely simulate actual sex, harness and phallus combinations were developed so that one sex partner may wear the phallus and otherwise perform almost as if the phallus was the partner's own erect penis. The typical harness consisted of a trapezoidal or rectangular patch of inelastic clothlike material such as rubber or leather, with elastic straps attached to the corners of the patch. The patch measured approximately 3" by 4" and had a hole in its center through which the phallus was inserted. After the phallus was inserted through the hole of the patch, the harness was put on by the user by placing the elastic straps around the legs and/or waist. The phallus was made of substantially rigid plastic and was completely hollowed out to make room for the insertion of a male partner's real penis (and depending upon the size of the phallus, there would be room for either a flaccid or erect penis). The phallus was made hollow also to reduce the weight of the phallus so that it did not cause the elastic to stretch out. The back of the phallus was fitted with a flange extending outward from the circumference of the phallus, perpendicularly to the axis of the phallus. The flange would extend outward from about 0.5" to about 1.5" to prevent the phallus from slipping through the hold in the patch. (Some phalluses had the elastic straps attached directly to the phallus' flange, thereby eliminating the clothlike patch.) The phallus was held in place by the user's body pressing the harness patch against the phallus flange.

Another lesser used design was a three piece unit phallus, harness and a snap plate that works the same as the above except there are snaps to the front plate of the harness. Elastic or other straps fused in or snapped to the phallus base are also known.

These prior art devices have several drawbacks. Among them are the discomfort a user feels when wearing the harness, the tendency of the elastic to stretch too much during use so that the phallus and the wearer become misaligned, and the fact that the hole in the patch can only accommodate a narrow range of phallus diameters (i.e., a phallus with too large a diameter would not fit through the hole in the patch, and a phallus with too narrow a diameter would slip about in the patch).

In addition, the prior art harnesses would not work well with the more modern phalluses which are made of dense, resilient rubberlike material which more closely replicate the look and feel of erect real penises. That is because the weight of the phallus would be too great for the elastic straps, and during use of the harness and phallus during sex, the resilient phallus is likely to bend too much.

SUMMARY OF THE INVENTION

The subject invention is a phallus or other device formed of substantially resilient material in combination with a plug formed of a substantially rigid material. The plug is preferably approximately 20% to 70% of the length of the phallus or other receiving device. The phallus or other device has a hollow shaped hole in its back which corresponds in shape to the shape of the plug, but has slightly smaller dimensions. In use the plug is forced into the device's hollow back. Air is forced out of the hollow and a vacuum-like fit is achieved between the device and the plug. The plug and device may be combined with a harness formed preferably of inelastic clothlike material forming the body of the harness, the body having a length sufficient to reach around from the wearer's lower abdomen, between the wearer's legs and up onto or over the wearer's buttocks. Inelastic straps may be attached along the ends of the harness body and are adjustably attachable to each other so that the harness may be worn somewhat like a bathing suit bottom which has fasteners on the sides. The harness body has a sufficient width at its central portion to avoid binding the wearer, and gradually widens toward each of its ends. The portion of the harness body which would be positioned below the wearer's abdomen has a hole formed in it and means for fastening to a flange formed in the back of the plug. In use the plug is passed through the hole in the harness body and the plug's flange is attached thereto. The plug is then forced into the hollow of the phallus or other device. Then the harness is put on by the wearer to enable the wearer to simulate sex or otherwise use such other device's.

Another aspect of the present invention is use of the plug device in a system wherein there are a variety of plug receiving devices which are interchangeable with the phallic device.

DETAILED DESCRIPTION OF THE INVENTION

Figure 1:
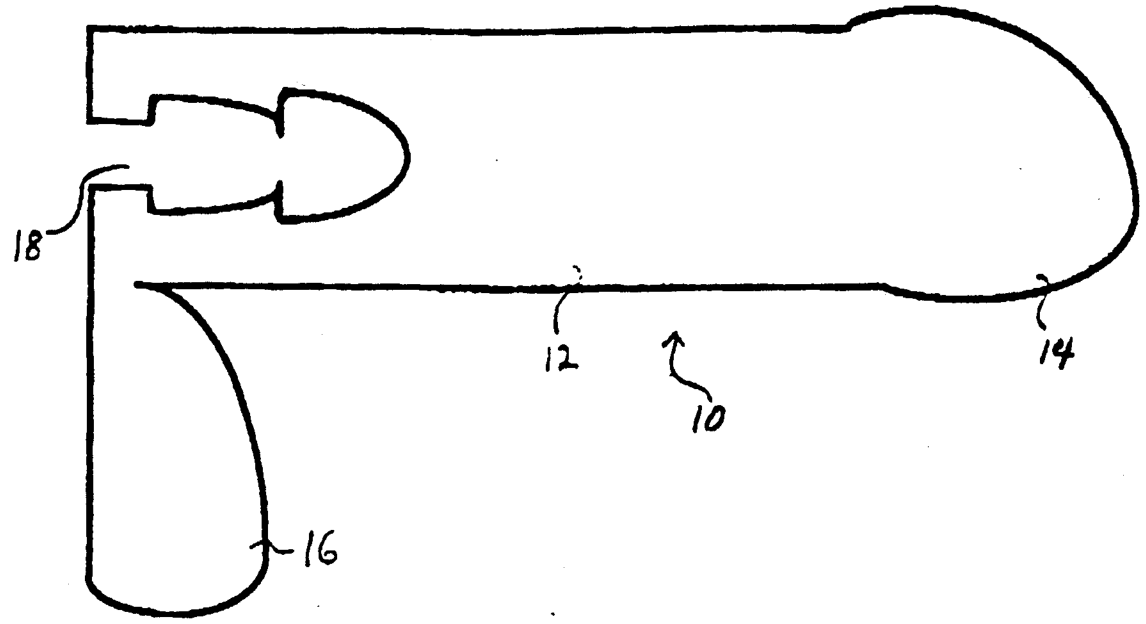
FIG. 1 is the side cross-sectional view of the phallus portion of the invention, viewed along the middle of the phallus from the right side.

The subject invention is illustrated in the attached drawings which are referred to herein. The same reference numeral will be used to identify identical elements throughout the drawings.

Referring to FIG. 1, the phallus portion 10 of the invention is shown in cross-section. The phallus is formed in a mold and comprises resilient, rubberlike material preferably such as polyvinyl chloride. In the preferred embodiment the phallus is formed in two "pours." The first pour forms the outer portion of the phallus. When that has set, the inner surface of the first pour is dusted with talcum powder and the second pour is made forming the interior of the phallus. The polyvinyl chloride of the second pour is slightly less resilient than the polyvinyl chloride of the first pour and the talcum powder dusting causes the first and second pours to only partially adhere to each other. As a result the phallus approximates the feel of the outer skin of an erect real penis. However, the double pour method is not necessary to obtain the results of the invention and the invention is described in connection with the single pour method of making the phallus.

Figure 6:
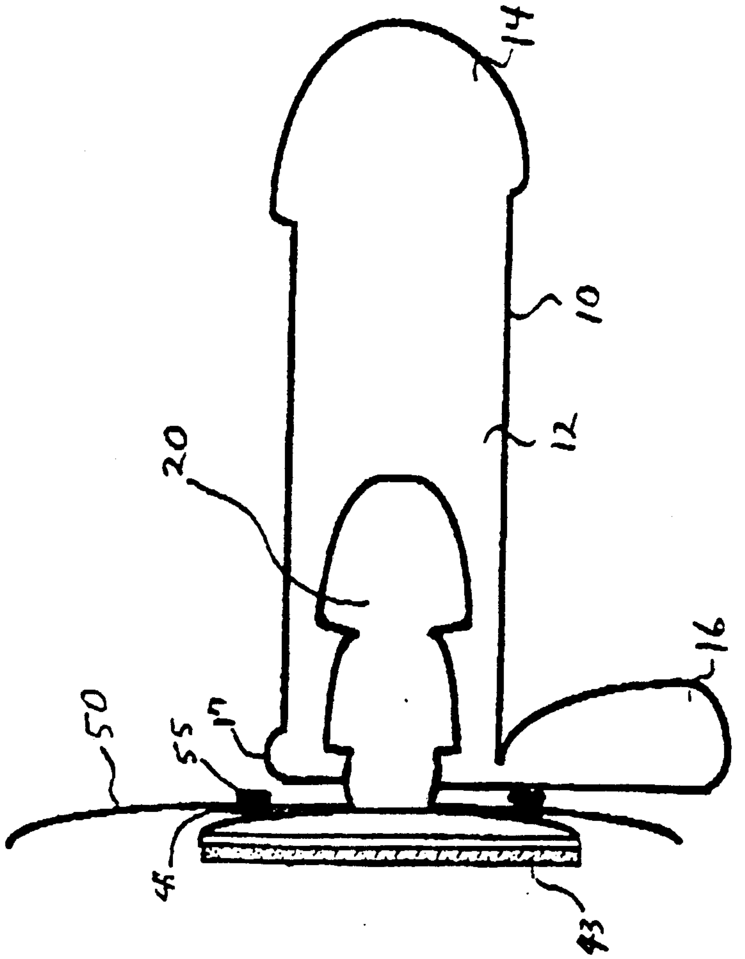
FIG. 6 is the side cross-sectional view of the phallus combined with the plug and harness (shown partially), viewed along the middle of the combination from the right side.
Figure 7:
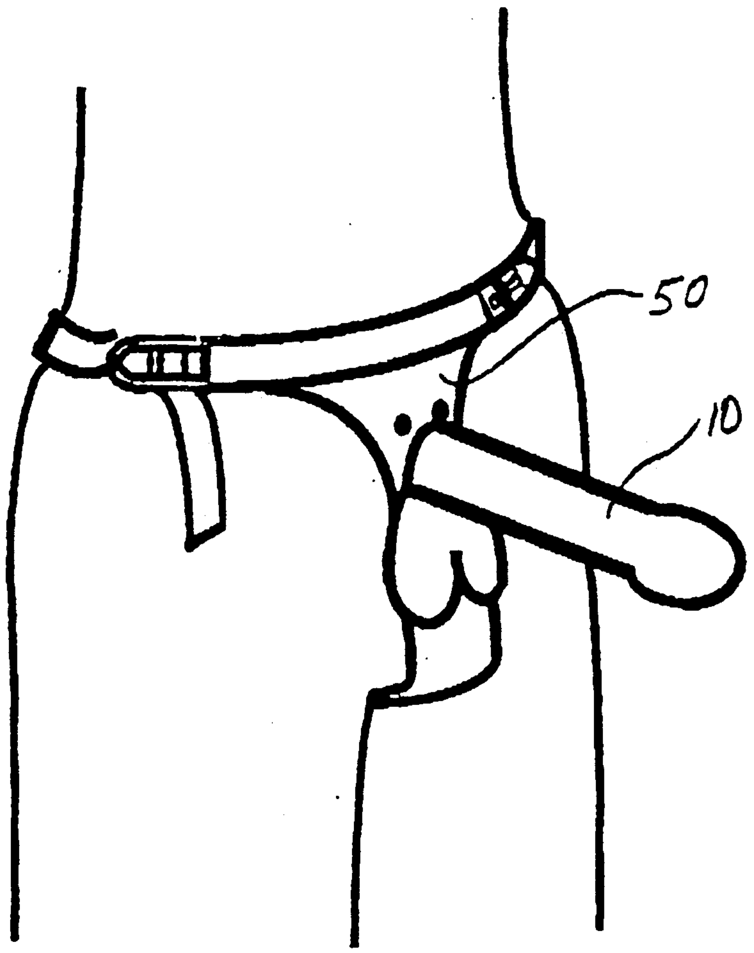
FIG. 7 is a perspective view of the phallus, harness and plug (which is not visible) as worn by a person.

Immediately after the polyvinyl forming the phallus is poured, an insert is positioned in the mold so that a hollow 18 is formed in the back end of the phallus (comprised of shaft 12, and in the ornamental embodiment of the phallus illustrated in FIGS. 1, 6 and 7, glans 14 and scrotum 16). After the polyvinyl chloride has set, the insert is removed from the back of the phallus and the phallus is removed from the mold. Typically, though not necessarily, the phallus is approximately circular in cross-section when viewed along the longitudinal axis of the phallus.

Figure 2:
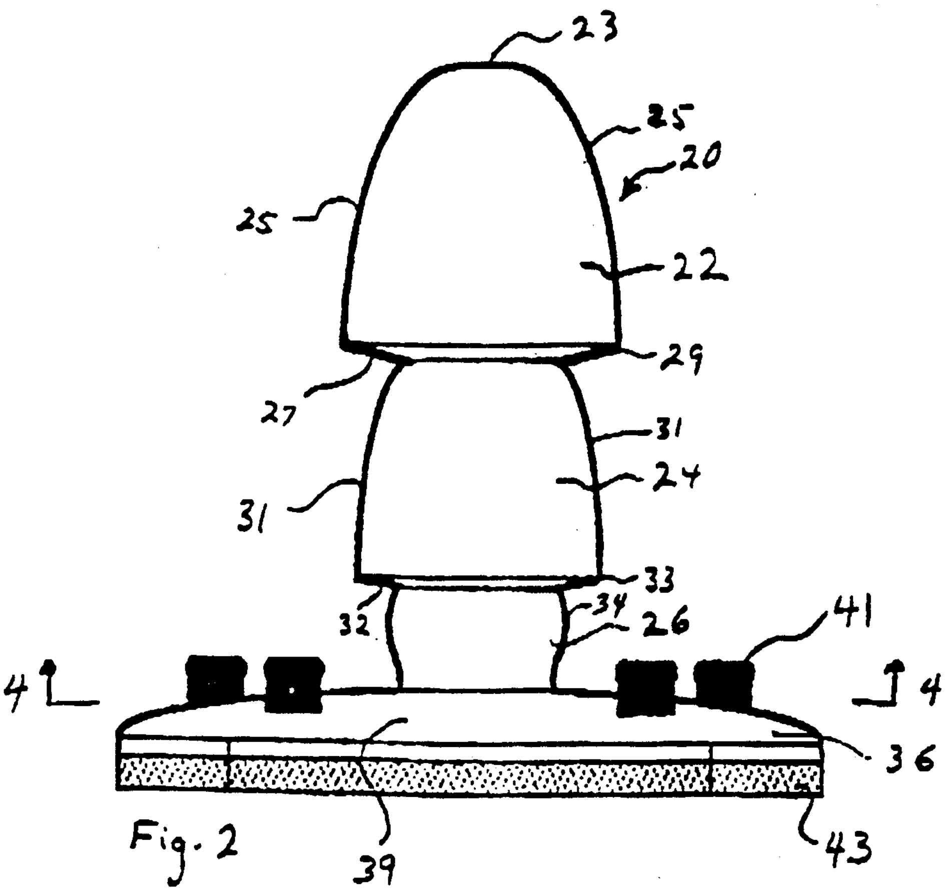
FIG. 2 is the bottom view of the plug portion of the invention.
Figure 3:
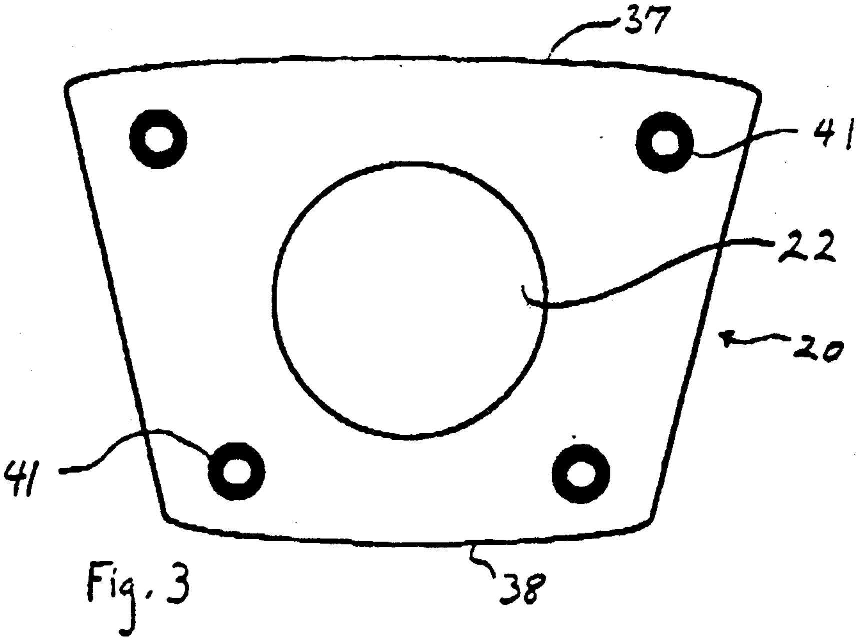
FIG. 3 is the front view of the plug portion of the invention.
Figure 4:
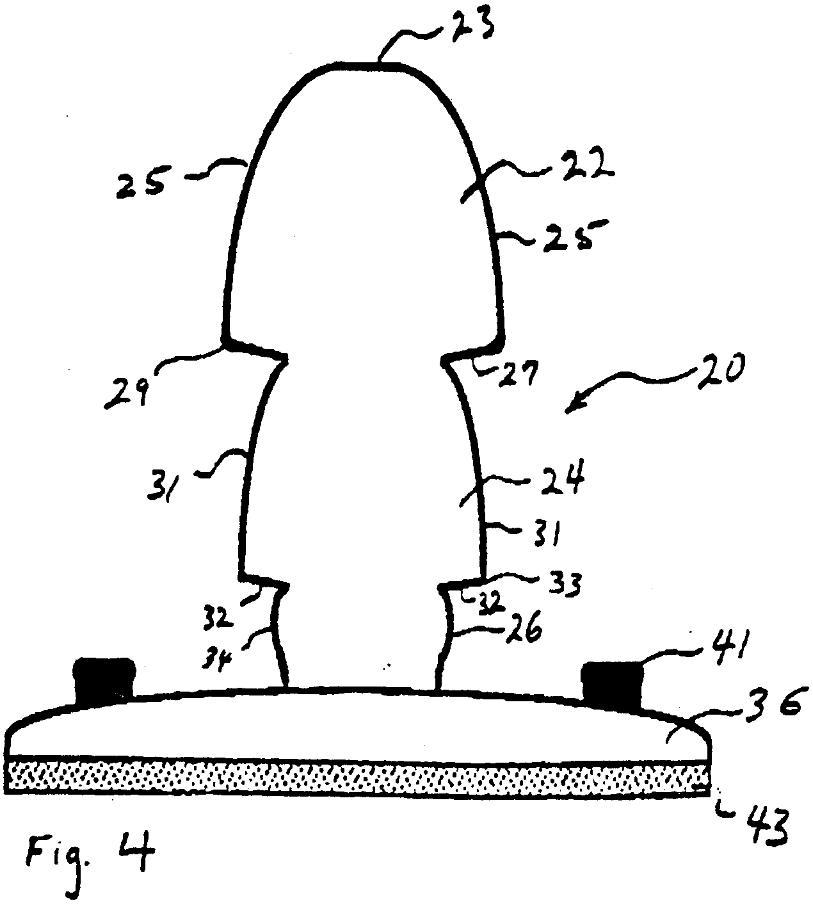
FIG. 4 is the cross-sectional view of the plug portion of the invention viewed from the bottom along lines 4—4 of FIG. 2.

Referring to FIGS. 2–4, the plug portion 20 of the invention is shown. The plug portion is also formed in a mold. The plug is preferably formed of plastisol, and is substantially rigid, having preferably a 50–100 durometer hardness. (100 is virtually absolutely rigid.) The optimal hardness is approximately 80 to allow some flexibility. This provides for safety when used by sexual partners and also makes the plug easier to pull from its mold in the manufacturing process.

The plug comprises three sections, head 22, middle section 24 and stem 26, each of which is typically, though not necessarily, approximately circular in cross-section when viewed along the longitudinal axis of the plug (which axis is substantially parallel to, if not coincident with, the longitudinal axis of the phallus). The head is bullet-shaped with a rounded, almost flat tip 23 and first side surface 25 curving first sharply then less sharply toward the back of the head section, like a parabola. First back surface 27 of the head section is formed so that it lies at an angle to the perpendicular to the longitudinal axis of the plug, with the innermost portion of first back surface 27 being closer to the back of the plug than the outermost portion of first back surface 27. First corner 29 at the juncture of first side surface 25 and first back surface 27 is slightly rounded.

Middle section 24 is immediately adjacent first back surface 27. The middle section is shaped like a bullet with its leading end cut off. The middle section's side surface (i.e., second side surface 31) curves toward the back of the plug parabolically. In the preferred embodiment the largest diameter of the middle section is slightly less than the largest diameter of the head section, and the back surface of the middle section (i.e., second back surface 32) is much closer to the perpendicular to the longitudinal axis of the plug than is first back surface 27 (but it is not undercut). Second corner 33 at the juncture of second side surface 31 and second back surface 32, is much less rounded than first corner 29.

The head and middle section could be shaped so that their cross-sections, when viewed from the side, are arrow-shaped, but that would not be preferred.

Stem 26 is immediately adjacent second back surface 32. Third surface 34 on stem 26 is convexly shaped toward the stem's leading end.

The head, middle and stem sections can all be molded integrally together. In the preferred embodiment a flange portion 36 is molded of plastisol integrally to the back of stem section 26. The flange is formed in the shape of a trapezoid with top edge 37 being wider than bottom edge 38. The forward most surface 39 of the flange is slightly crowned.

After the plug is pulled from its mold, the male portions 41 of snap fasteners are attached near the corners of the flange. To help assure that the snaps are attached to the same places on every plug, posts may be positioned in the plug mold which will make guide indentations in the forward most surface 39 of the flange.

In the final step in making the plug, a rubber backing 43 is adhered to the back of the plug.

Figure 5:
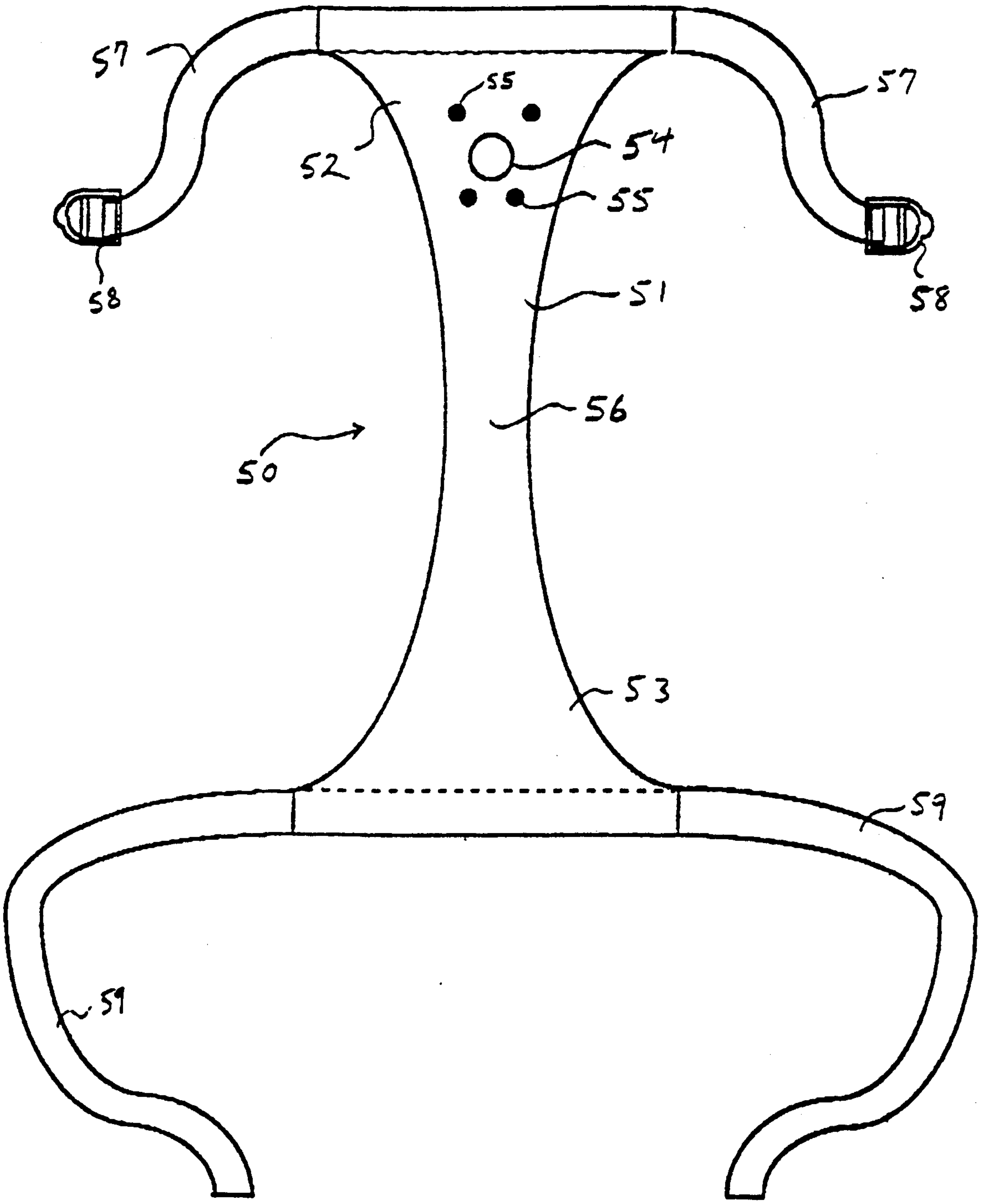
FIG. 5 is the plan view of the harness used with the plug and phallus.

In FIG. 5 a harness 50 is illustrated which is used in combination with the plug and phallus. The harness has an inelastic clothlike body 51, which in the preferred embodiment is formed of cloth-backed vinyl. The harness can also be from leather, rubber and other materials.

Body 51 has a front end 52, a back end 53 and a central portion 56. At the front end 52 are disposed inelastic straps 57 which terminate at buckles 58. At back end 53 are disposed inelastic straps 59. The harness body is sufficiently long to reach around from the wearer's lower abdomen, between the wearer's legs and up onto or over the wearer's buttocks. Straps 57 and 59 are adjustably attachable to each other through buckles 58 so that the harness may be worn somewhat like a bathing suit bottom which has fasteners on the sides. The harness body has a sufficient width at its central portion 56 to avoid binding the wearer, and gradually widens toward each of its ends. Front end 52 of the harness body, which would be positioned below the wearer's abdomen, has a hole 54 formed in it and female portions 55 of snap fasteners are positioned about hole 54 so that they will align with male snap fasteners portions 41 on the plug.

In use the plug is passed through the hole in the harness. (The size of the hole is not important so long as the plug can fit through it.) The plug's flange is then attached to the harness body by means of the male and female portions, 41 and 55, respectively, of the snap fasteners, and then the plug is forced into the hollow of the phallus, as illustrated in FIG. 6 (wherein the phallus is shown with additional ornamental ridge 17). Then the harness is put on by the wearer, as shown in FIG. 7, to enable the wearer to simulate sex.

With reference to FIGS. 1-4 and 6, hollow 18 has the same shape as plug 20, but has slightly smaller dimensions. This helps form the airtight fit. The tip 23 of plug head 22 is rounded for safety purposes and to help expel air as the plug is being pushed into the phallus' hollow. First corner 29 is likewise rounded to help force air from the hollow. Second corner 33 is not rounded and second back surface 32 is given an almost vertical angle to provide the greatest frictional resistance where it is most useful, toward the back of the phallus. In addition, the tip 23 and back surfaces 27 and 32 may be given a rough texture in the molding process to increase the frictional grip on the interior surface of the phallus, thereby helping to decrease unwanted play between the phallus and the plug.

The double air lock brought about by the use of both the head and middle sections of the plug is very helpful in maintaining the vacuum-like grip between the phallus and plug, particularly during vigorous sexual activity. And, during such activity the structure of the harness and the trapezoidal shape of the plug's flange increase comfort. In addition, the flange's rubber backing provides resilient cushioning to the wearer.

The plug should preferably be between 20% and 70% of the length of the phallus, and optimally about 40% of its length. It is most necessary to have rigidity toward the rear end of the phallus where the most torque would be experienced. Also, for safety reasons the plug should not be too long compared to the overall length of the phallus. The glans portion of erect real penis is not as rigid as the rest of the penis so that there will be less likelihood of injury being inflicted upon a sexual partner. Similarly, the forward-most portion of the phallus should not be made too rigid for the same reason.

In a preferred embodiment, the phallus is about 8" long and the plug is about 3" long. The widest diameter of the head of the plug is about 1.25". The widest diameter of the plug's stem is about 0.75". The top edge of the flange is about 3" and the bottom edge is about 2". The side edges of the flange are about 2.5" each. The harness is about 21" long, its central portion is about 2.5" wide, and its front and back ends are each about 8.5" wide.

Preferably, the harness straps include friction buckles for secure, non-slip movement, with the straps designed to fit waists up to 44".

To release the plug from the phallus, the back end of the phallus should be pulled outward to allow air to enter into the hollow while the plug is pulled out in a corkscrew motion. The release is made easier if before use the interior of the phallus' hollow is lightly dusted with talcum powder.

All the components of the invention are washable and the invention is of great benefit to those needing a prosthesis or desiring to keep their sexual activities disease free.

Above there has been described a unique phallus and plug combination. It will be understood that various other changes of the details, materials, steps, arrangements of parts, and uses, which have been herein described and illustrated in order to explain the nature of the invention, will occur to and may be made by those skilled in the art, upon a reading of this disclosure, and such changes are intended to be included within the principles and scope of this invention.

By way of example, greater rigidity of the resilient phalluses described herein is desired even if the phallus is hand held. In such event, the plug can be molded integrally with a handle which could be substituted for the flange. The handle would prevent excess wear and tear on hand held phalluses. Also, if an extra long phallus is used, the head of the plug may be elongated and shaped to conform to any bends molded into the phallus.

Figure 8:
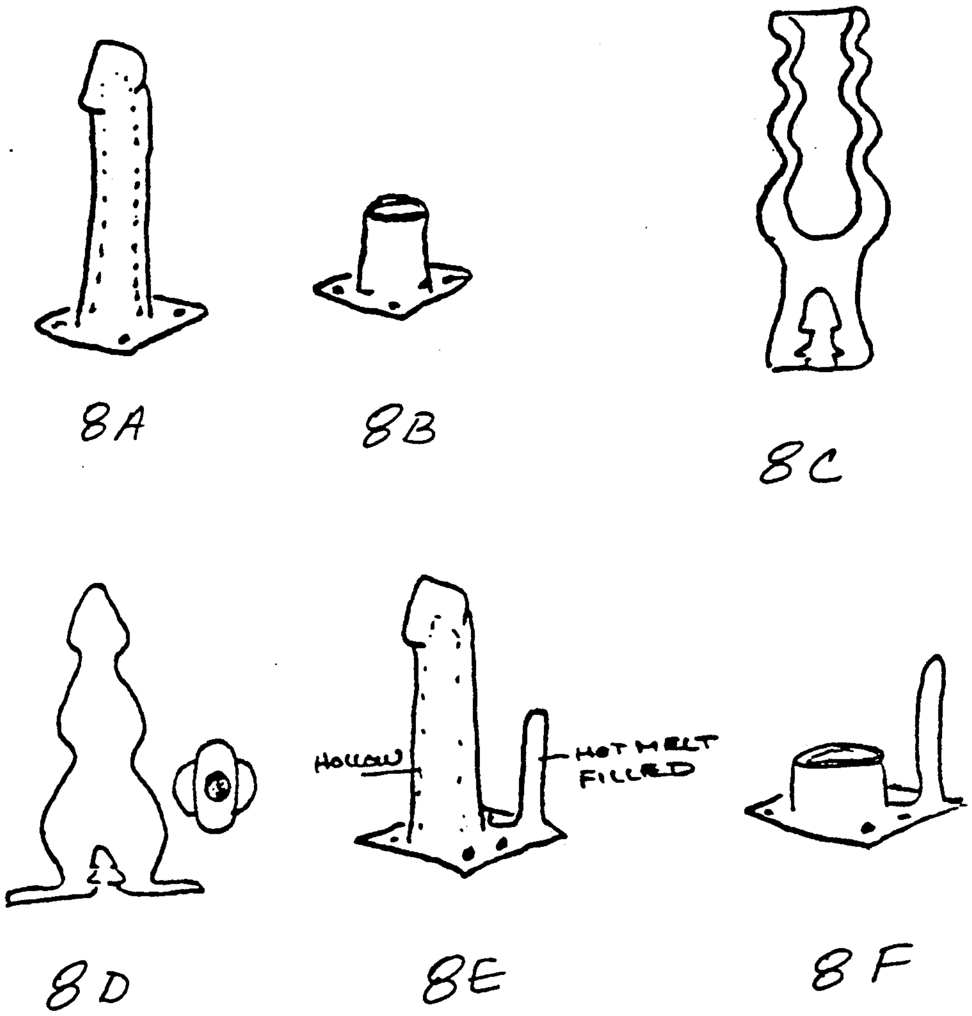
FIGS. 8*a*–8*f* are perspective views of devices other than a phallus which can be used with the plug and harness components of the present invention.

As another example, plug receiving devices other than phalluses can also be used, with particular reference to FIG. 8, a hollow phallus (8A), a hollow splint (8B), a device which can receive a penis (8C cross section), and other shaped phalluses, splints and combination devices (8D (cross section), 8E and 8F). Thus the plug of the present invention can be used with all of these devices or other such plug receiving components interchangeably.

Figure 9:
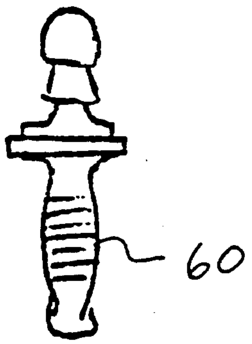
FIG. 9 is a perspective view of the plug portion of the invention with a handle thereon.
Figure 10:
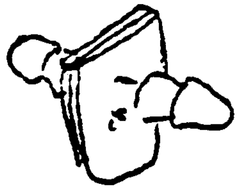
FIG. 10 is a perspective view of two plug portions attached back to back.

FIG. 9 shows the plug portion which is attached to a handle 60 rather than a harness. FIG. 10 shows two plug portions attached back to back.

I claim:

1. A combination phallus and plug device, wherein said plug comprises, from front to rear, a head section and a middle section, with said middle section being disposed immediately adjacent and behind said head section, wherein the largest cross-sectional area of said head section perpendicular to the longitudinal axis extending from said head section through said middle section is larger than the largest cross-sectional area of said middle section perpendicular to said longitudinal axis, and wherein said phallus has a hollow formed in its back, said hollow corresponding in shape to said plug and having slightly smaller dimensions than said plug, whereby said plug may be fitted into said hollow in the same direction as said longitudinal axis, with said head section being inserted first.

2. A combination phallus and plug device, wherein said plug is formed of a substantially rigid material, in a shape having a front and a rear, the plug comprising, from front to rear, a head, middle section and stem disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and wherein said phallus is formed of a substantially resilient material and has a hollow formed in its back, said hollow corresponding in shape to said plug and having slightly smaller dimensions than said plug, whereby said plug may be fitted into said hollow in the same direction as said longitudinal axis, with said head section being inserted first.

3. The phallus and plug device of claim 2 wherein each of said head and middle section is substantially bullet-shaped.

4. The phallus and plug device of claim 3 wherein said phallus is formed of a solid, flexible and elastic material.

5. The phallus and plug device of claim 4 wherein said solid, flexible and elastic material is polyvinyl chloride.

6. The phallus and plug device of claim 4 wherein said hollow formed in the back of said phallus and said plug are so configured that when the plug is fitted into said hollow air is forced out of it and a substantially airtight seal is formed between the plug and the interior surface of said phallus along said hollow.

7. The phallus and plug device of claim 6 wherein said head of said plug has a first back surface disposed such that the cross-sectional area perpendicular to said longitudinal axis of the front-most portion of said first back surface is greater than that of the rear-most portion of said first back surface.

8. The phallus and plug device of claim 7 wherein said middle section of said plug has a second back surface disposed either perpendicular to said longitudinal axis or such that the cross-sectional area perpendicular to said longitudinal axis of the front-most portion of said second back surface is greater than that of the rearmost portion of said second back surface.

9. The phallus and plug device of claim 6 wherein the length of said plug is approximately 20% to 70% of the length of said phallus.

10. The phallus and plug device of claim 6 wherein said plug has a flange extending outward from the rear of said stem, said phallus and plug device further comprising a harness intended to be worn by a human, which harness has an inelastic body, said body having a front end, a back end and a central portion, and inelastic straps attached along the ends of the harness body which are adjustably attachable to each other so that the harness may be worn like a bathing suit bottom having fasteners on the sides, said harness body being sufficiently long to reach around from the wearer's lower abdomen, between the wearer's legs and up onto the wearer's buttocks, said harness body being narrowest at its central portion yet having a sufficient width at its central portion to avoid binding the wearer, said front end of the harness body which would be positioned below the wearer's abdomen having a hole formed in it through which the head portion of the plug may be inserted before said plug is fitted into said hollow in said phallus, and said front end of the harness body comprising means for detachably attaching said body to said flange on said plug.

11. The phallus and plug device of claim 6, wherein said substantially rigid material of which said plug is formed is plastisol having a durometer hardness of approximately 50–100.

12. A combination phallus and plug, wherein said phallus is formed of a substantially resilient material and said plug is formed of a substantially rigid material, wherein said plug is comprised of a head portion and a stem disposed immediately adjacent and behind said head portion, said head portion having a longitudinal axis extending from the head portion through said stem, said head having a cross-sectional area perpendicular to said longitudinal axis which is greater than the cross-sectional area perpendicular to said longitudinal axis of said stem, said phallus having a hollow formed in its back and corresponding in shape to said plug so that said plug may be fitted into said hollow in the same direction as said longitudinal axis, with said head section being inserted first.

13. The combination of claim 1 wherein the plug is substantially rigid.

14. The combination of claim 1 wherein the phallus is formed of a substantially resilient material.

15. A plug device, wherein said plug device is formed of a substantially rigid material in a shape having a front and rear, the plug comprising, from front to rear, a head, middle section and stem disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem.

16. The plug device of claim 15 wherein said head of said plug has a first back surface disposed such that the cross-sectional area perpendicular to said longitudinal axis of the front-most portion of said first back surface is greater than that of the rearmost portion of said first back surface.

17. The plug device of claim 16 wherein said middle section of said plug has a second back surface disposed either perpendicular to said longitudinal axis or such that the cross-sectional area perpendicular to said longitudinal axis of the front-most portion of said second back surface is greater than that of the rearmost portion of said second back surface.

18. A phallus device, wherein said phallus is formed of a substantially resilient material in a shape having a front and a rear and has a hollow formed in its back, said hollow having, from front to rear, a head, middle section and stem section disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem.

19. The phallus device of claim 18 wherein each of said head and middle section is substantially bullet-shaped.

20. The plug device of claim 15 wherein there are two such plug devices connected to each other such that the head portions oppose each other.

21. The combination of claim 1, wherein said plug additionally comprises a stem section, said stem section being disposed immediately adjacent and behind said middle section, and wherein said largest cross-sectional area of said middle section is larger than the largest cross-sectional area of said stem section perpendicular to said longitudinal axis.

22. A combination phallus and plug device, wherein said plug is formed of a substantially rigid material in a shape having a front and a rear, the plug comprising, from front to rear, a head, middle section and stem disposed one behind the other in that order substantially along the same longitudinal axis, said head and middle section each having a substantially bullet shape and tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and wherein said phallus is formed of a substantially resilient material and has a hollow formed in its back, said hollow corresponding in shape to said plug and having slightly smaller dimensions than said plug, whereby said plug may be fitted into said hollow in the same direction as said longitudinal axis, with said head section being inserted first; and wherein said phallus is formed of a solid, flexible and elastic material.

23. The phallus and plug device of claim 22 wherein said solid, flexible and elastic material is polyvinyl chloride.

24. The phallus and plug device of claim 22 wherein said hollow formed in the back of said phallus and said plug are so configured that when the plug is fitted into said hollow air is forced out of it and a substantially airtight seal is formed between the plug and the interior surface of said phallus along said hollow; and wherein said plug has a flange extending outward from the rear of said stem, said phallus and plug device further comprising a harness intended to be worn by a human, which harness has an inelastic body, said body having a front end, a back end and a central portion, and inelastic straps attached along the ends of the harness body which are adjustably attachable to each other so that the harness may be worn like a bathing suit bottom having fasteners on the sides, said harness body being sufficiently long to reach around from a wearer's lower abdomen, between the wearer's legs and up onto the wearer's buttocks, said harness body being narrowest at its central portion yet having a sufficient width at its central portion to avoid binding the wearer, said front end of the harness body which would be positioned below the wearer's abdomen having a hole formed in it through which the head portion of the plug may be inserted before said plug is fitted into said hollow in said phallus, and said front end of the harness body comprising means for detachably attaching said body to said flange on said plug.

25. The phallus and plug device of claim 22 wherein said hollow formed in the back of said phallus and said plug are so configured that when the plug is fitted into said hollow air is forced out of it and a substantially airtight seal is formed between the plug and the interior surface of said phallus along said hollow; and wherein said substantially rigid material of which said plug is formed is plastisol having a durometer hardness of approximately 50–100.

26. A plug device, wherein said plug device is formed of a substantially rigid material in a shape having a front and a rear, the plug comprising, from front to rear, a head, middle section and stem disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and wherein said substantially rigid material of which said plug is formed is plastisol having a durometer of approximately 50–100.

27. A plug device, wherein said plug device is formed of a substantially rigid material in a shape having a front and a rear, comprising, from front to rear, a head, middle section and stem disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and wherein said plug has a flange extending outward from the rear of said stem, said plug device further comprising a harness intended to be worn by a human, which harness has an inelastic body, said body having a front end, a back end and a central portion, and inelastic straps attached along the ends of the harness body which are adjustably attachable to each other so that the harness may be worn like a bathing suit bottom having fasteners on the sides, said harness body being sufficiently long to reach around from the wearer's lower abdomen, between the wearer's legs and up onto the wearer's buttocks, said harness body being narrowest at its central portion yet having a sufficient width at its central portion to avoid binding the wearer, said front end of the harness body which would be positioned below the wearer's abdomen having a hole formed in it through which the head portion of the plug may be inserted, and said front end of the harness body comprising means for detachably attaching said body to said flange on said plug.

28. A phallus device, wherein said phallus is formed of a substantially resilient material in a shape having a front and a rear and has a hollow formed in its back, said hollow having, from front to rear, a head, middle section and stem section disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and wherein said phallus is formed of a rubberlike material.

29. The phallus device of claim 28, wherein said rubberlike material is polyvinyl chloride.

30. A plug device, wherein said plug device is formed of a substantially rigid material in a shape having a front and a rear, the plug comprising, from front to rear, a head, middle section and stem disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and further including a handle connected to the device adjacent to the stem portion.

31. A plug assembly comprising at least two plug devices, wherein each plug device is formed of a substantially rigid material in a shape having a front and a rear, comprising, from front to rear, a head, middle section and stem disposed one behind the other in that order substantially along the same longitudinal axis, said head and middle section each tapering outwardly from the front toward the rear, with the largest cross-sectional area perpendicular to said longitudinal axis of said head being larger than the largest cross-sectional area perpendicular to said longitudinal axis of said middle section and with the largest cross-sectional area perpendicular to said longitudinal axis of said middle section being larger than the largest cross-sectional area perpendicular to said longitudinal axis of said stem; and wherein the at least two such plug devices are connected to each other such that the head portions oppose each other.

* * * * *